United States Patent [19]
Mawby

[11] Patent Number: 5,900,944
[45] Date of Patent: May 4, 1999

[54] METHOD AND DEVICE FOR THE ANALYSIS OF PESTICIDES

[75] Inventor: Andrea Mawby, Cleveland, Ohio

[73] Assignee: Day-Glo Color Corp., Cleveland, Ohio

[21] Appl. No.: 08/810,484

[22] Filed: Mar. 3, 1997

[51] Int. Cl.$^6$ ....................................................... G01J 3/46
[52] U.S. Cl. ............................................................ 356/425
[58] Field of Search ............................................. 356/425

[56] References Cited

U.S. PATENT DOCUMENTS

| | | | |
|---|---|---|---|
| 4,201,791 | 5/1980 | Livaudais, Jr. et al. | 424/358 |
| 4,368,591 | 1/1983 | Barke et al. | 47/57.6 |
| 4,411,989 | 10/1983 | Grow | 435/20 |
| 4,975,364 | 12/1990 | Taylor et al. | 435/4 |

OTHER PUBLICATIONS

Specification Sheet Hach DR700 Portable Colorimeter.
Specification Sheet Hitachi Instruments, Inc. F–4500 Fluorescene Spectrophotometer.

Primary Examiner—Robert Kim
Assistant Examiner—Zandra V. Smith
Attorney, Agent, or Firm—Calfee, Halter & Griswold LLP

[57] ABSTRACT

The present invention provides methods and devices for the quantitative analysis of pesticides with fluorescent pigments. The methods include dry mode, fluid mode, and in-field quantitative pesticide analysis. The methods also include dry mode and fluid mode data acquisition procedure by which linear relationships between spectral data and quantity of pesticide may be determined. The devices include a first and a second pesticide analysis device. The first pesticide analysis device includes a spectrophotometer and logic for determining the amount of pesticide present in a sample. The second pesticide analysis device also includes a spectrophotometer and logic for determining the amount of pesticide present in a sample. The second pesticide analysis device is further configured for in-field quantitative pesticide analysis of samples.

20 Claims, 8 Drawing Sheets

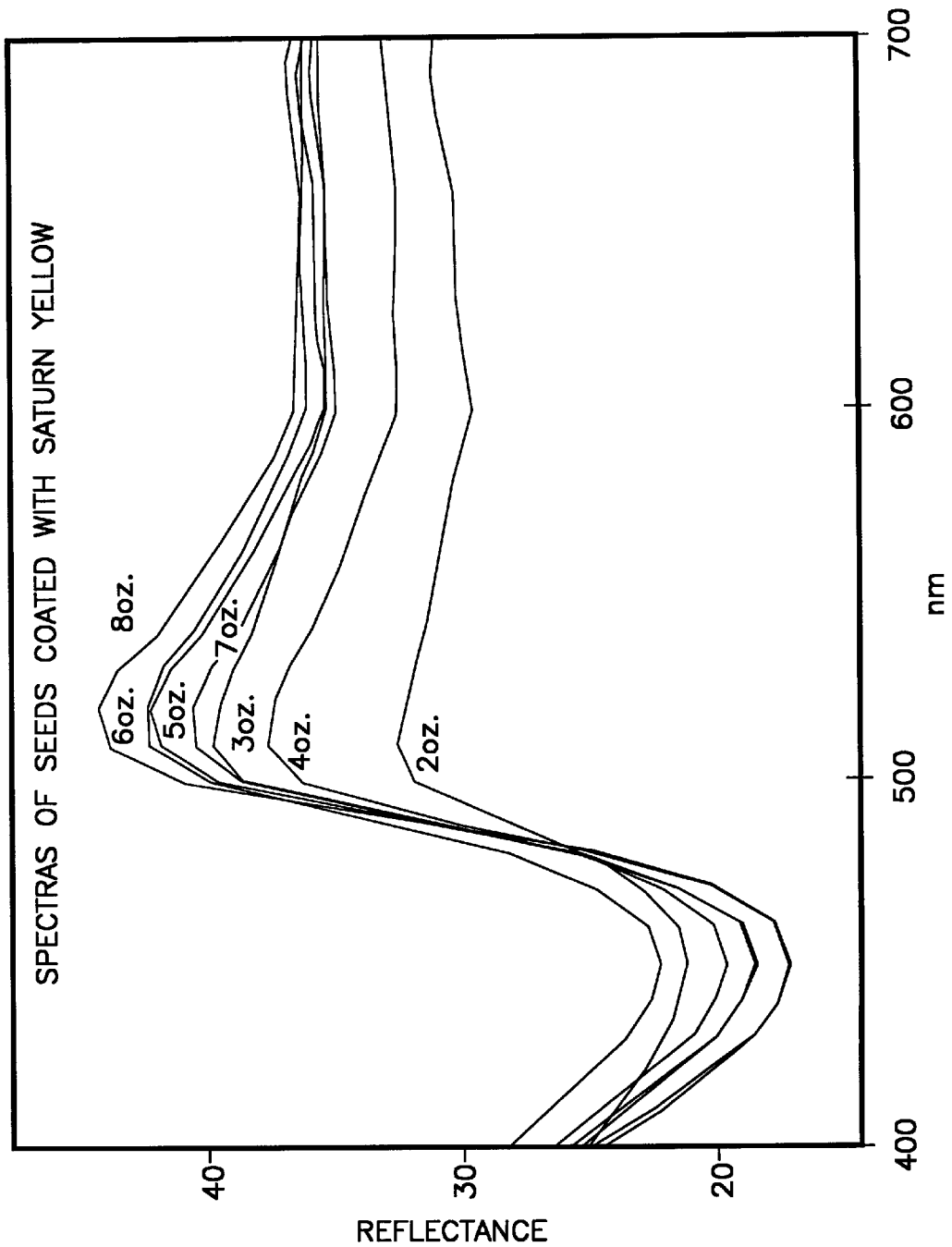

| ENTER YOUR DELTA C VALUE: | 17.29 | 23.80 | 29.32 | 31.71 | 35.52 |
|---|---|---|---|---|---|
| MINOLTA MAGENTA-B 96C10 (-WHITE) | 1.77 | 3.19 | 4.39 | 4.91 | 5.74 |
| ACTUAL VALUE | 2.00 | 3.00 | 4.00 | 5.00 | 6.00 |
| %ERROR | 11.73 | 6.21 | 9.78 | 1.74 | 4.26 |
| | | | | | |
| ENTER YOUR DELTA C VALUE: | 15.62 | 21.63 | 25.55 | 28.93 | 30.89 |
| MINOLTA SATURN-B 96C10 (-WHITE) | 1.76 | 3.24 | 4.21 | 5.04 | 5.53 |
| ACTUAL VALUE | 2.00 | 3.00 | 4.00 | 5.00 | 6.00 |
| %ERROR | 12.03 | 8.08 | 5.24 | 0.88 | 7.87 |
| | | | | | |
| ENTER YOUR DELTA C VALUE: | 12.30 | 15.30 | 19.62 | 22.13 | 26.72 |
| MINOLTA ORANGE-B 96C10 (-WHITE) | 1.76 | 2.91 | 4.11 | 4.81 | 6.09 |
| ACTUAL VALUE | 2.00 | 3.00 | 4.00 | 5.00 | 6.00 |
| %ERROR | 12.03 | 2.99 | 2.83 | 3.76 | 1.49 |
| | | | | | |
| ENTER YOUR DELTA C VALUE: | 14.82 | 18.87 | 22.09 | 26.44 | 28.53 |
| MINOLTA MAGENTA-A 96C10 (-BLACK) | 1.95 | 3.03 | 3.99 | 5.22 | 5.81 |
| ACTUAL VALUE | 2.00 | 3.00 | 4.00 | 5.00 | 6.00 |
| %ERROR | 2.66 | 1.04 | 0.14 | 4.39 | 3.20 |
| | | | | | |
| ENTER YOUR DELTA C VALUE: | 11.55 | 18.24 | 19.61 | 23.97 | 27.34 |
| MINOLTA SATURN-A 96C10 (-BLACK) | 1.92 | 3.11 | 3.97 | 6.07 | 5.93 |
| ACTUAL VALUE | 2.00 | 3.00 | 4.00 | 5.00 | 6.00 |
| %ERROR | 3.88 | 3.73 | 0.84 | 1.45 | 1.22 |
| | | | | | |
| ENTER YOUR DELTA C VALUE: | 5.85 | 10.42 | 15.55 | 17.64 | 20.87 |
| MINOLTA ORANGE-A 96C10 (-BLACK) | 1.85 | 3.04 | 4.39 | 4.94 | 5.78 |
| ACTUAL VALUE | 2.00 | 3.00 | 4.00 | 5.00 | 6.00 |
| %ERROR | 7.74 | 1.46 | 9.73 | 1.25 | 3.59 |

Fig.9

METHOD AND DEVICE FOR THE ANALYSIS OF PESTICIDES

FIELD OF THE INVENTION

The invention relates generally to a method and device for pesticide analysis, and, more particularly, to methods and devices for determining a quantity pesticide in a sample via spectral analysis of the sample.

BACKGROUND OF THE INVENTION

The determination of pesticide quantities in agricultural and environmental practices is very important. A pesticide is, broadly speaking, an agent used to control pests, such as insects. In the agricultural area, pesticides are employed in a variety of ways including coating seeds to prevent the seeds from being consumed before they are planted. However, it is desirable to control the quantity pesticide used to control pests because of possible unwanted effects to other animals and the environment. Therefore, in controlling the amount of pesticide used it is important to accurately determine the quantity of pesticide present in a given sample.

The current art of quantitative pesticide determination includes the use of liquid and gas chromatography. Generally, in liquid chromatography, a sample seed is ground up from which a liquid extract is taken. The extract is filtered and then placed in a high performance liquid chromatography system or gas chromatography system.

Liquid and gas chromatography, however, have several disadvantages. First, they require very controlled environments and highly skilled trained personal which are not suitable to industrial application areas. Second, they require numerous highly controlled steps and expensive equipment which requires a high level of maintenance. Thirdly, they are not readily adaptable for in-field analysis of pesticide levels. Therefore, methods and devices which overcome these disadvantages are desirable.

SUMMARY OF THE INVENTION

According to the present invention, simple methods and devices are provided for the quantitative analysis of pesticides.

A method for determining the quantity of pesticide in a plurality of seeds is provided which comprises the steps of: illuminating a plurality of seeds which include a coating having a pesticide and a pigment mixture; detecting the light reflected from the illuminated pigment mixture; and relating the light reflected from the illuminated pigment mixture to a quantity of pesticide. The method in an alternate embodiment further comprises the step of removing the pigment from a plurality of seeds having a coating that comprises a pesticide and a pigment by adding a solvent to the plurality of seeds. The step of illuminating the seeds employs electromagnetic radiation having a frequency within the range of 200–800 nm, preferably 400 to 700 nm. The step of relating the light reflected from the illuminated pigment mixture to a quantity of pesticide comprises the step of determining a color saturation level of the light reflected from the illuminated pigment mixture and relating the color saturation level of the light reflected from the illuminated pigment mixture to a quantity of pesticide.

The present invention also provides a method for determining the relationship between a quantity of pigment and a quantity of pesticide, the method comprising the steps of: mixing a known quantity of pigment with a known quantity of pesticide; applying the mixture to a seed sample; removing a substantial amount of the pigment from the plurality of seeds, preferably by dissolving the solvent, determining a quantity of pigment from the removed amount of pigment; and determining a quantity of pesticide from the determined quantity of pigment. The step of determining a quantity of pigment from the removed amount of pigment comprises the step of determining a color saturation level of the removed amount of pigment. Preferably illuminating the removed pigment with electromagnetic radiation having a frequency of 400–700 nm and detecting the light therefrom.

The present invention further provides a device for determining the amount of pesticide in a sample, the device comprising: computer hardware for the input, output and processing of digital and analog signals; a light source for emitting electromagnetic radiation; a light detector for detecting electromagnetic radiation; and logic for determining the amount of pesticide in a sample. The logic for determining the amount of pesticide in a sample is included within a removable memory device and comprises logic for determining a color saturation level of the sample. The logic for determining the amount of pesticide an a sample further comprises logic for relating the color saturation level to a quantity of pigment and logic for relating the quantity of pigment to a quantity of pesticide.

It is therefore an advantage of the present invention to provide simple, cost-effective, accurate methods and devices for the quantitative analysis of pesticides.

It is a further advantage of this invention to provide methods and devices which are configured for in-field quantitative analysis of pesticides.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

FIG. 2 is a graph illustrating the reflectance of SATURN YELLOW™ pigment on dry seed samples, having different ratios of pesticide to pigment, in the 400–700 nm wavelength range;

FIG. 9 illustrates a table of experimental data obtained by dry mode pesticide analysis procedure on cotton seeds for the SATURN YELLOW™, FIRE ORANGE™ and CORONA MAGENTA™ pigmenys.

DETAILED DESCRIPTION OF ILLUSTRATED EMBODIMENT

Figure 1A:
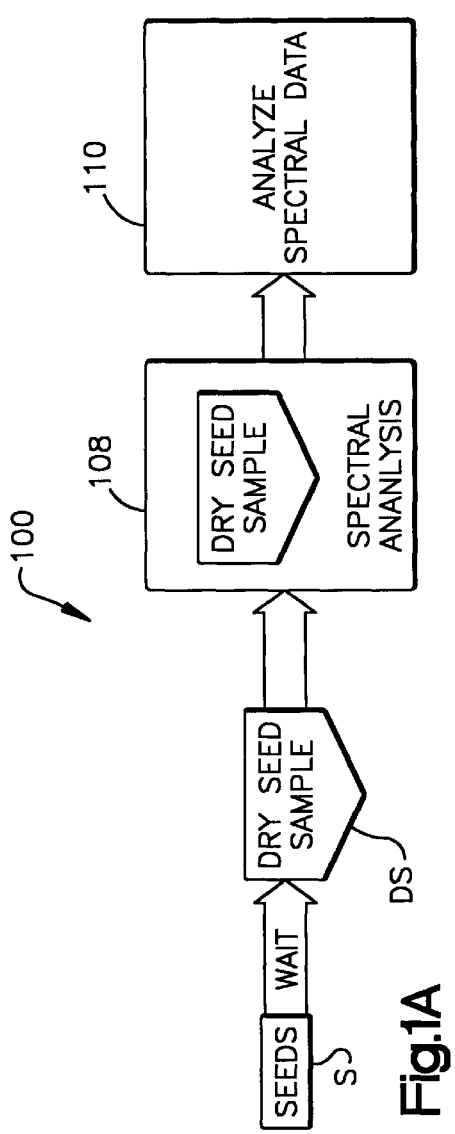
FIG. 1A is a high-level functional block diagram of a dry mode pesticide analysis procedure.
Figure 1B:
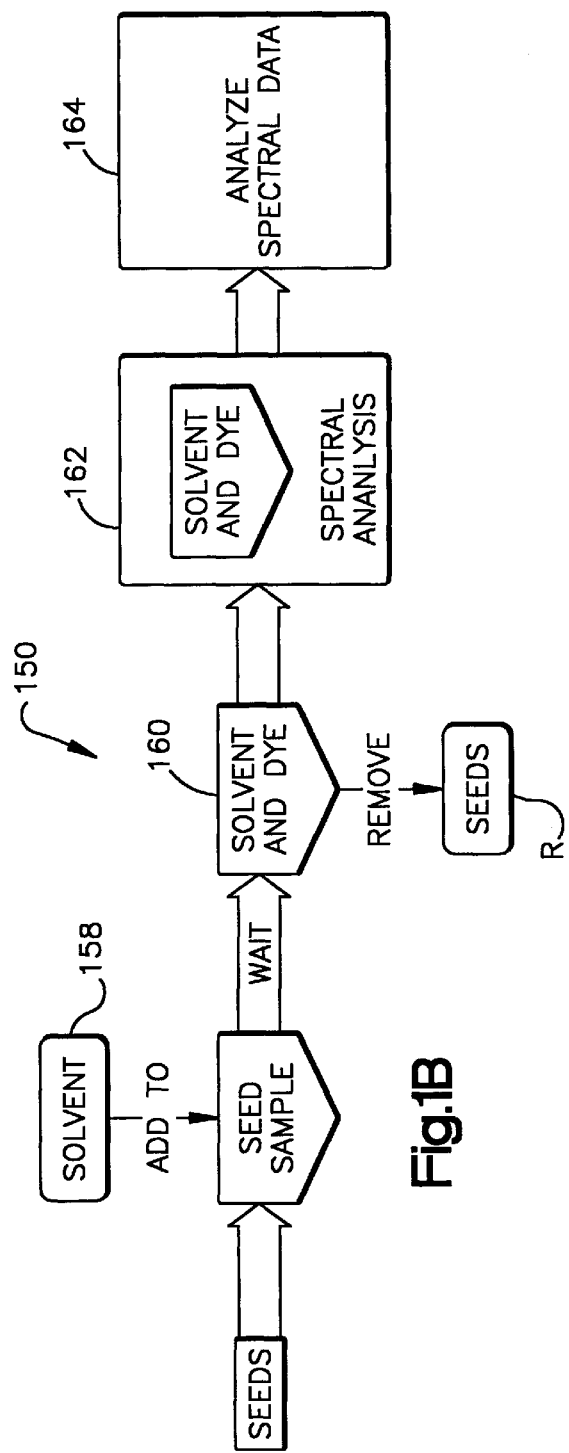
FIG. 1B is a high-level functional block diagram of a fluid mode pesticide analysis procedure.

Referring now to the drawings, and for the present to FIG. 1A and 1B, a high-level functional block diagrams of a dry mode pesticide analysis procedure and a fluid mode pesticide analysis procedure of the present invention are, respectively, shown. The fundamental steps illustrated in FIGS. 1A and 1B, which will be presently described, are exemplary of a pesticide analysis and data acquisition procedure used for establishing relational data between a quantity of fluorescent pigment and a quantity of pesticide. They are also illustrative of the method and operation of two embodiments of a pesticide analysis device that includes the relational data.

Fluorecent Colorants

The fluorescent colorants employed in the methods include fluorescent pigments and fluorescent dyes. The fluorescent pigments are preferred. The fluorescent colorant preferably has been approved for agricultural use by governmental agencies.

The fluorescent pigments comprise a polymer and a fluorescent dye. Suitable fluorescent pigments include, for example, those disclosed and claimed in U.S. Pat. No. 5,215,679 issued Mar. 15, 1994, and U.S. Pat. No. 5,294,664 which are specifically incorporated herein by reference. Preferably the fluorescent pigment is an aqueous dispersion.

A suitable fluorescent pigment is a fluorescent orange pigment which comprises an acrylonitrile styrene polymer commercially available as "EPX 15 Blaze Orange™ pigment" from Day-Glo® Color Corp., Cleveland, Ohio. Other suitable fluorescent pigments include, for example "Fire Orange™" a red orange pigment, "Rocket Red™" a red pigment, "Aurora Pink®" a pink pigment, "Corona Magenta™" a red pigment, and "Arc Yellow™", a yellow pigment, Saturn Yellow™, a yellow pigment, Signal Green™, a green pigment, Horizan Blue™, a blue pigment, all of which are available from Day-Glo® Color Corp. These pigments fluoresce under ultra-violet light as well as in daylight.

The preferred pigments have the following composition: a water insoluble polymer comprising at least four monomers, at least one monomer selected from each of the following groups (i) through (iv); from about 40% to about 80%, preferably about 52% to about 65% total polymer weight of water insoluble vinyl monomer free of polar groups; from about 15% to about 35%, preferably about 25% to about 35%, total polymer weight of vinyl nitrile; from about 1.5% to about 4.5% total polymer weight of vinyl monomer containing sulfonate groups; from about 5% to about 20%, preferably about 5% to about 15%, total polymer weight of polar vinyl monomer selected from the group consisting of: polar acrylate esters, polar methacrylate esters, vinyl acetate, a substituted acrylamide containing hydroxyl or carboxylic ester groups, and mixtures thereof; and fluorescent dye. The fluorescent dye is present in an amount sufficient to impart fluorescent color to the pigment.

Most preferably the fluorescent pigment comprises: styrene as the water insoluble non polar vinyl monomer; sodium 2-acrylamido-2-methylpropane-sulfonate as the vinyl monomer containing sulfonate groups; hydroxypropyl methacrylate as the polar vinyl monomer; and acrylonitrile as the vinyl nitrile.

Preferably the fluorescent pigment is an aqueous dispersion so that water is present in an amount to provide a total solids content of from about 0.5% to less than 100%. Suitable fluorescent dyes include conventional dyes such as fluorescent type dyes belong to the dye families known as rhodamines, fluoresciens, coumarins, naphthalimides, benzoxanthenes, acridines, and azos. Suitable fluorescent dyes include, for example, Basic Yellow 40, Basic Red 1, Basic Violet 11, Basic Violet 10, Basic Violet 16, Acid Yellow 73, Acid Yellow 184, Acid Red 50, Acid Red 52, Solvent Yellow 44, Solvent Yellow 131, Solvent Yellow 135, and Solvent Yellow 160. The fluorescent dyes comprise from about 0.1 to 15% of the total weight of the pigment. One or more fluorescent dyes are present in the fluorescent pigment. The fluorescent dyes, alone that is, without a polymer carrier, are less preferred colorants.

Pesticide Analysis: Dry Mode.

Referring now to FIG. 1A in particular, a high-level functional block diagram of a dry mode pesticide analysis procedure 100 for establishing relational data is shown. A seed sprayer mixes a quantity, preferably a known quantity of pesticide with a fluorescent colorant, preferably a known quantity to form a pesticide/pigment mixture. The pesticide typically includes a polymer which promotes uniform coating. The fluorescent pigment comprises a pigment and a polymeric pigment carrier that is incorporated into an EPX® emulsion system. It is believed that the fluorescent pigment physically bonds to the matrix of the polymer. One such mixture is that of GOUCHO®, a pesticide, and SATURN YELLOW™.

The dry seed sample D is placed in a glass container which is then placed in optical communication 108 with a pesticide analysis device (to be described) for spectral analysis. The quantity of seeds in the dry seed sample D, will depend on the size of the glass container. It is preferable that the amount of seeds in the dry seed sample D be of an amount sufficient to ensure that all of the light, or a substantial portion thereof, is incident on the seed sample in the glass container. The term optical communication is hereby defined to include any means or method which allows for the transmission and/or reflectance of electromagnetic radiation or electrical signals (e.g., digital or analog) which represent the transmission and/or reflectance of electromagnetic radiation.

The spectral analysis 108 includes the pesticide analysis device emitting white light incident on the dried seed sample D and detecting the reflected light from the dry seed sample D. The detected light is in a range of 400–700 nm. Once the dry seed sample has been illuminated and the reflected light detected, an analysis 110 of the spectral data to determine reflectance and color saturation data is performed by the pesticide analysis device. Color saturation is the concentration of spectral power distribution at a given wavelength. Generally, the higher the spectral power distrubition is at a given wavelength, the more saturated will be the associated color. The analysis of the spectral data employs certain linear relationships between color saturation and the amount of pigment/pigment present on the seeds. The technician is then given a displayed output which indicates the quantity of pesticide present in the sample. The technician would preferably perform this analysis several times (i.e. 5 times) so that a statistical average is relied upon rather a single reading of the sample. Thereafter, the technician may determine what is the proper corrective action, if any, required.

Pesticide Analysis: In Field Dry Mode.

The pesticide analysis method and the second illustrated embodiment (shown in FIG. 6B and described below) allows a technician to perform an in-field dry mode pesticide analysis on growing vegetation out in the field. The spectral analysis of a leaf or other piece of vegetation having a quantity of fluorescent pigment/pesticide present on it may simple be performed by causing light from a light source, either directly or indirectly via fiber optics, to be incident on the leaf. The reflected light would be detected by a light detector, either directly or indirectly via fiber optics. The second illustrated embodiment (FIG. 6B) includes a probe unit that is capable of being placed directly on, or in very close proximity to the leaf. The reflected light, or its digital or analog electrical equivalent would then be transmitted to the computer hardware within the second illustrated embodiment of the pesticide analysis device for analysis by the QS logic. While the in-field dry mode pesticide analysis has been described with respect to a leaf, it may be also be applied to seeds, soil, fertilizers, papers, etc.

Pesticide Analysis: Fluid Mode.

Referring now to FIG. 1B, a high-level functional block diagram of a fluid mode pesticide analysis procedure 150. The seeds are coated as described in the dry mode pesticide analysis 100. A known amount of solvent 158 is added to the seed sample CS so that the pigment which is present on the seed sample is removed. Suitable solvents include for example, organic solvents such as methanol. The seeds R are removed from the solvent and pigment mixture 160 and the solvent and pigment mixture 160 is placed in a cuvette which is then placed in a spectrophotometer for spectral analysis 162, according to conventional methods.

The spectral analysis 162 includes the pesticide analysis device emitting white light incident on the solvent and pigment mixture and detecting the transmitted light therefrom. The detected light is in a range of 400–700 nm. Once the solvent and pigment mixture has been illuminated and the transmitted light detected, an analysis 164 of the spectral data is performed to determine absorbance and color saturation data by the pesticide analysis device. The analysis of the spectral data employs certain linear relationships between color saturation and the amount of pigment present on in the solvent and pigment mixture or the seeds. The technician is then given a displayed output which indicates the quantity of pesticide present in the sample. The technician would preferably perform this analysis several times (i.e. 5 times) so that a statistical average is relied upon rather a single reading of the sample. Thereafter, the technician may determine what is the proper corrective action, if any, required.

Data Acquistion: Dry Mode.

The manner of establishing the linear relationships between color saturation and quantity of pigment or pigment will now be employing a dry mode data acquisition procedure. The dry mode data acquisition procedure includes series of spectral tests on seeds samples having differing ratios of pesticide to pigment. Referring now to FIG. 1A, a known quantity of pesticide is mixed with a known quantity of fluorescent colorant, that is a pigment, to form a first pesticide/pigment mixture. As was described above, the fluorescent colorant preferably has been approved for agricultural use by governmental agencies. The pesticide is incorporated into a polymer which promotes uniform coating. It is believed that the fluorescent pigment physically bonds to the matrix of the polymer. The present discussion will focus on the use of SATURN YELLOW™, a fluorescent pigment manufactured by DAYGLO COLOR CORP. of Cleveland, Ohio, and the pesticide GOUCHO®, as applied to cotton seeds.

The pesticide/pigment mixture is deposited on a plurality of seeds S such that the seeds are coated with a quantity of pesticide/pigment mixture. A dry seed sample D is collected for analysis. The dry seed sample D is placed in a glass container which is then placed in optical communication 108 with a pesticide analysis device (to be described) for spectral analysis. The quantity of seeds in the dry seed sample D will depend on the size of the glass container. It is preferable that the amount of seeds in the dry seed sample D be of an amount sufficient to ensure that all of the light, or a substantial portion thereof, is incident on the seed sample in the glass container.

The spectral analysis 108 includes the pesticide analysis device emitting white light incident on the dried seed sample D and detecting the reflected light from the dry seed sample D. The detected light is in a range of 400–700 nm. Once the dry seed sample has been illuminated and the reflected light detected, an analysis 110 of the spectral data to determine reflectance and color saturation data is performed by the pesticide analysis device. These steps are repeated with a second, third, fourth, etc. mixture of known pesticide quantity to known pigment quantity, with all other factors held constant. Each pesticide/pigment mixture should be analyzed more than once (at least five time) so as to employ a statistical average in the final analysis of the mixture. In this manner, one may derive relational data between color saturation and quantity of pesticide.

Figure 3:
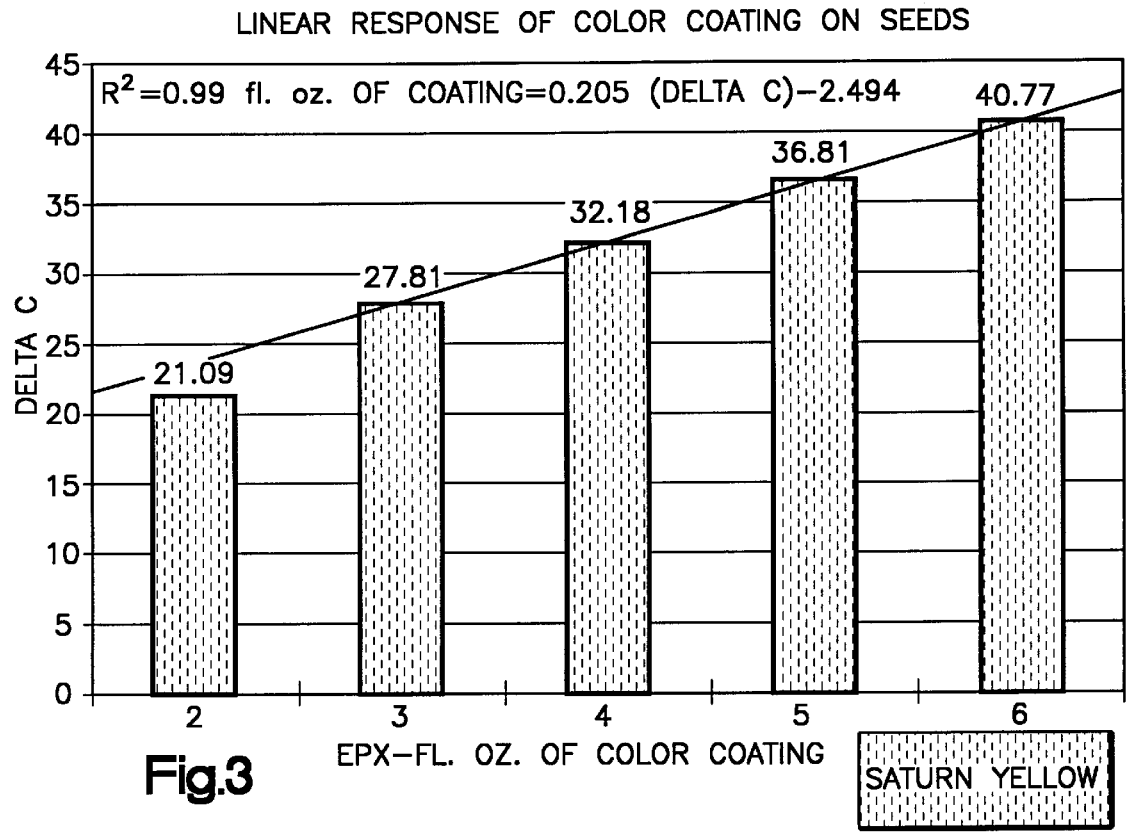
FIG. 3 is a graph showing the fluid ounces of SATURN YELLOW™ pigment on the x-axis and the corresponding color saturation (shown as "delta C") on the y-axis.

Illustrated in FIGS. 2 and 3 are the spectral data for derived for SATURN YELLOW™ pigment pigment. More specifically, FIG. 2 is a graph illustrating the reflectance of dry seed samples, having different ratios of pesticide to pigment, in the 400–700 nm wavelength range. From this reflectance data, tristimulus values are generated which, in turn, allow for the generation of CIE (Commission Internationale de L'Eclairage) L* a* b* uniform color space data. The tristimulus values are the amounts of three matching lights, in a given trichromatic system, that are required to match the shade of color under consideration. The CIE L* a* b* uniform color space data is defined by equations (1a), (1b) and (1c):

$$L* = 116\left(\frac{Y}{Y_0}\right)^{1/3} - 16 \text{ for } \frac{Y}{Y_0} > 0.008856 \quad (1a)$$

$$a* = \left[\left(\frac{X}{X_0}\right)^{1/3} - \left(\frac{Y}{Y_0}\right)^{1/3}\right] \text{ for } \frac{X}{X_0} > 0.008856 \quad (1b)$$

$$b* = \left[\left(\frac{Y}{Y_0}\right)^{1/3} - \left(\frac{Z}{Z_0}\right)^{1/3}\right] \text{ for } \frac{Z}{Z_0} > 0.008856 \quad (1c)$$

Where X, Y, Z and $X_0$, $Y_0$, $Z_0$ are the tristimulus values of the sample and the light source or illuminant, respectively. From the CIE L* a* b* uniform color space data, the color saturation $C^{*ab}$ (or "delta C" sometimes hereinafter) is determined from equation (2A):

$$C^{*ab} = \sqrt{a^{*2} + b^{*2}} \quad (2A)$$

The conversion of reflectance data to tristimulus data, tristimulus data to CIE L* a* b* uniform color space data and the determination of color saturation based on CIE L* a* b* uniform color space data is conventional. See the AATCC (American Association of Textile Chemists and Colorists) Technical Manual, Vol. 68 (1993). Moreover, one may also analyze the spectral data for hue. Hue is the attribute of a visual sensation according to which an area appears to be similar to one of the perceived colors of red, yellow, green and blue, or a combination of any two of them. The hue can be determined by equation (2B):

$$h_{ab} = \tan^{-1}\left(\frac{b^*}{a^*}\right) \quad (2B)$$

Additionally, one may also employ the color difference value of B as defined by equation (2C):

$$E^{Lab} = \sqrt{L^{*2} + a^{*2} + b^{*2}} \quad (2C)$$

to derive a relationship between color difference and quantity of pesticide. The color difference is defined as a number defining the total color difference in the color space of a sample from a standard. Therefore, the manner of analysis of the present invention should not be limited to the determination of color saturation but may, in combination or in the alternative, be extended to color hue and color difference.

Illustrated in FIG. 3 is a graph showing the fluid ounces of SATURN YELLOW™ pigment on the x-axis and the corresponding color saturation (shown as "delta C") on the y-axis. The color saturation was determined from equation (2A) for each sample having a different ratio of pesticide to pigment. From the graph of FIG. 3, it can be seen that the relationship between fluid ounces of pigment (i.e., SATURN YELLOW™ pigment) and color saturation is approximately linear. This relationship may be approximated by the following linear equation (3):

Fluid ounces of SATURN YELLOW™ pigment=0.205 (delta C)−2.494     (3)

Once the amount of SATURN YELLOW™ pigment is obtained, the amount of pesticide can be determined based on the original pesticide to pigment (or pigment) ratio. Therefore, given the linear approximation formula relating color saturation of the seed coating to the amount of fluorescent pigment/pigment coating on the seeds, one can accurately determine the amount of pesticide present on the seeds.

Figure 4:
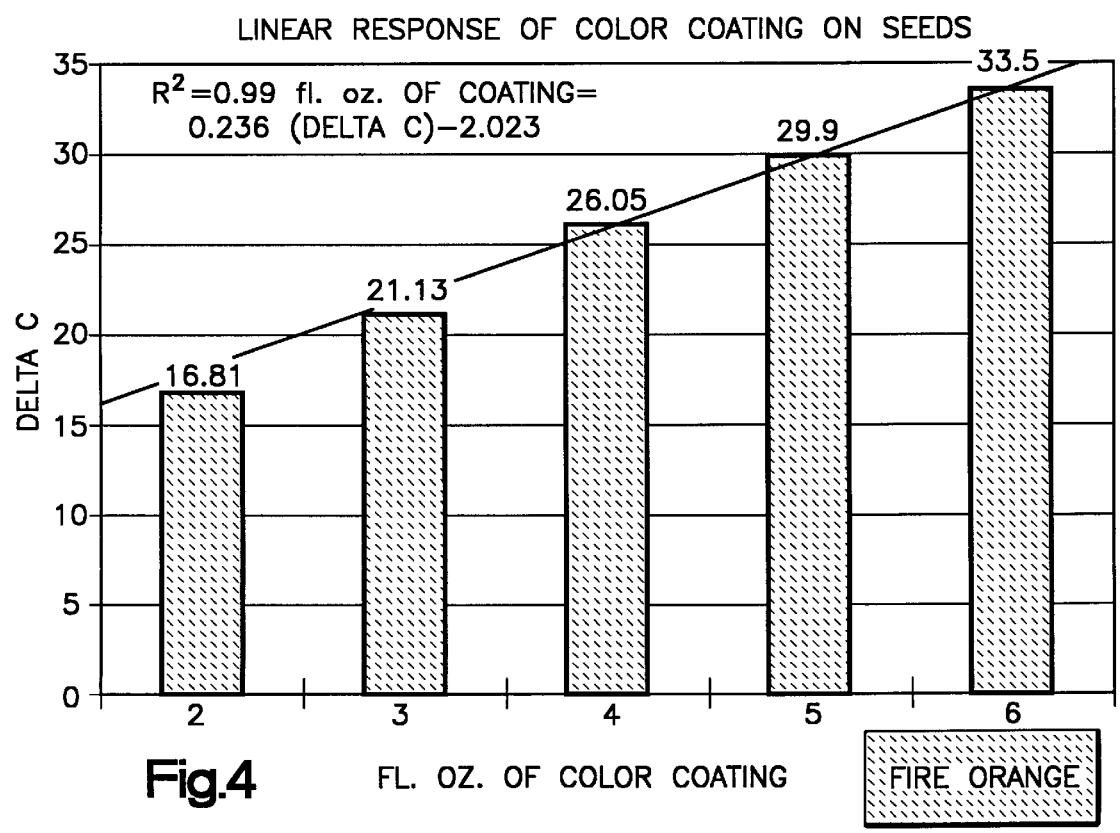
FIG. 4 is a graph illustrating the fluid ounces of FIRE ORANGE™ pigment on the x-axis and the correspond color saturation (shown as "delta C") on the y-axis.

The dry mode pesticide analysis procedure of FIG. 1A was also employed to determine the linear approximation between color saturation and other pigments. More particularly, FIG. 4 is a graph illustrating the fluid ounces of FIRE ORANGE™ pigment on the x-axis and the correspond color saturation (shown as "delta C") on the y-axis. From the graph of FIG. 4, it can be seen that the relationship between fluid ounces of FIRE ORANGE™ pigment and color saturation is also approximately linear. This relationship may be approximated by the following linear equation (4):

Fluid ounces of FIRE ORANGE™ pigment=0.236 (delta C)−2.023     (4)

Figure 5:
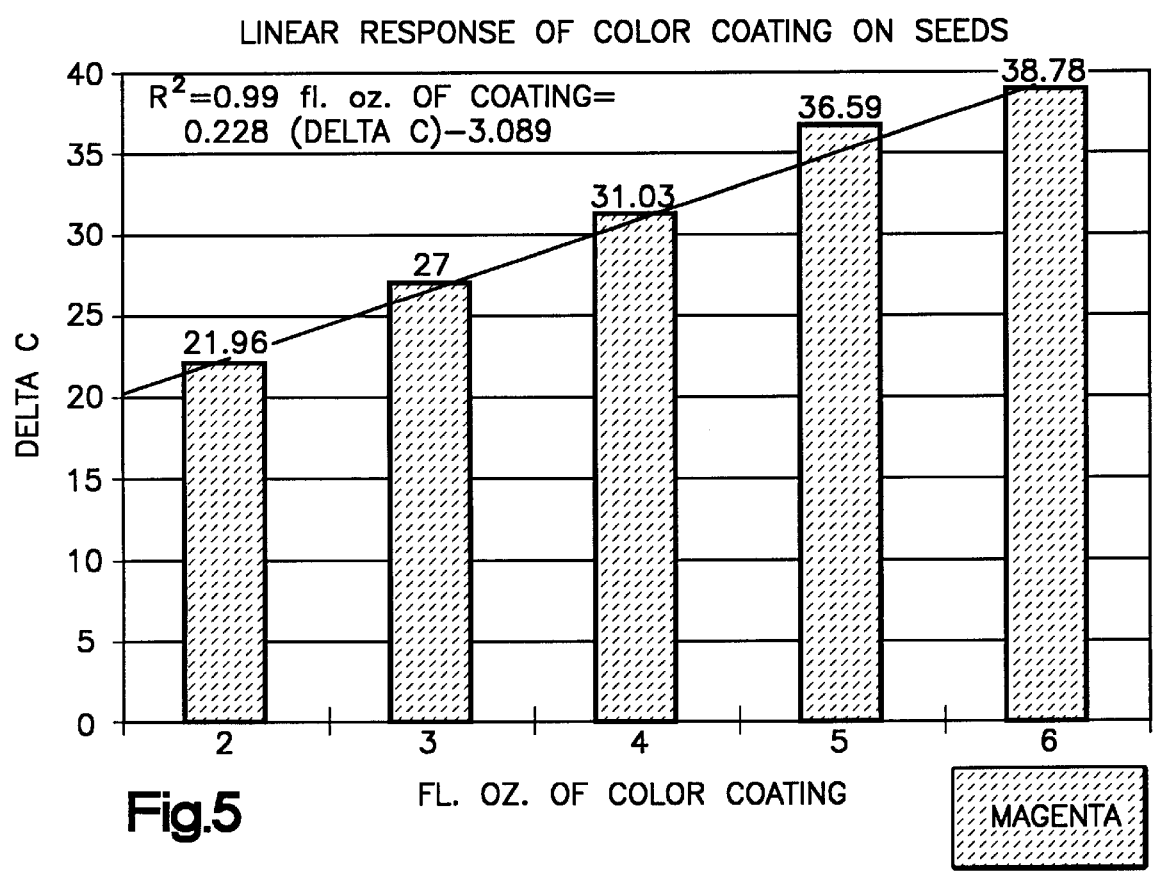
FIG. 5 is a graph illustrating the fluid ounces of CORONA MAGENTA™ pigment on the x-axis and the correspond color saturation (shown as "delta C") on the y-axis.

Shown in FIG. 5 is a graph illustrating the fluid ounces of CORONA MAGENTA™ pigment on the x-axis and the correspond color saturation (shown as "delta C") on the y-axis. From the graph of FIG. 5, it can also be seen that the relationship between the fluid ounces of CORONA MAGENTA™ pigment and color saturation is also approximately linear. This relationship may be approximate by the following linear equation (5):

Fluid ounces of CORONA MAGENTA™ pigment=0.228 (delta C)−3.089     (5)

Consequently, through the application of the above procedure to a plurality of ratioed pesticide/pigment mixtures, it is possible to derive relational data between the amount of pesticide present on a seed sample based on the color saturation data generated from a fluorescent coated seed sample. This relational data will depend on the particular type of seed, pesticide, pigment and test instrument used.

Data Acquisition: Fluid Mode.

The linear relationships between color saturation and quantity of pigment or pigment were also established by employing a fluid mode data acquisition procedure. The fluid mode data acquisition procedure includes a series of spectral tests on a solvent and pigment mixture derived from seeds samples having differing ratios of pesticide to pigment. Referring now to FIG. 1B, a known quantity of pesticide is mixed with a known quantity of fluorescent colorant, that is a pigment or pigment, to form a first pesticide/pigment mixture. The seeds are coated as described in the dry mode pesticide analysis 100.

A known amount of solvent 158 is added to the seed sample CS so that the pigment which is present on the seed sample may be removed. Suitable solvents include for example, organic solvents such as methanol. The seeds R are removed from the solvent and pigment mixture 160 and the solvent and pigment mixture 160 is placed in a cuvette which is then placed in a spectrophotometer for spectral analysis 162.

The spectral analysis 162 includes the pesticide analysis device emitting white light incident on the solvent and pigment mixture and detecting the transmitted light therefrom. The detected light is in a range of 400–700 nm. Once the solvent and pigment mixture has been illuminated and the transmitted light detected, an analysis 164 of the spectral data is performed to determine absorbence and color saturation data. These steps are repeated with a second, third, fourth, etc. mixture of known pesticide quantity to known pigment quantity, with all other factors held constant. Each pesticide/pigment mixture should be analyzed more than once (e.g., at least five times) so as to employ a statistical average in the final analysis of the mixture. In this manner, one may derive relational data similar to equations (3)–(5) between color saturation and quantity of pesticide or pigment.

In all of the Pesticide Analysis modes above, one may also employ other ranges of the electromagnetic spectrum. More specifically, the ultraviolet and infra-red light spectrums may be employed to derive the linear relationships above. Therefore, the effective range of detected light may be within the ultra-violet, visible and infra-red frequency ranges of 200–800 nm. However, it may be possible to extend the effective range of detected light into the near and middle infra-red wavelengths.

First Illustrated Embodiment of a Pesticide Analysis Device.

Figure 6A:
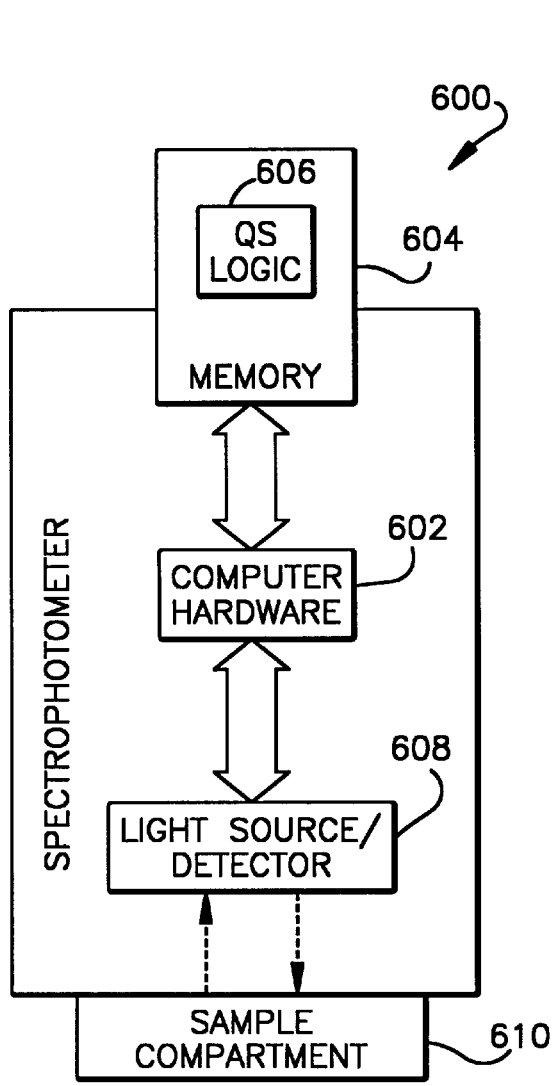
FIGS. 6A and 6B are two illustrated embodiments of a pesticide analysis device of the present invention.

Referring now to FIG. 6A, a pesticide analysis device 600 for the dry mode and fluid mode pesticide analysis of seeds is shown. The pesticide analysis device 600 includes a spectrophotometer having computer hardware 602, a memory 604 having Quantitative Sample logic 606 and a light source/detector device 608. The pesticide analysis device 600 also includes a sample compartment 610 which may be internal or external to the spectrophotometer. Spectrophotometers are conventional. Some manufacturers of suitable spectrophotometers includes the CM 508 D by Minolta Corporation and the Unispec™ Analysis System by PP Systems. Other available spectrophotometers include the Mini Scan XE 45/0 Spectrocolorimeter by Hunter Associates Laboratories, Inc. and the F4500 Fluorescence Spectrophotometer by Hitachi, LTD. A general description of the pesticide analysis device 600 and its components illustrated in FIG. 6A will now be discussed.

The computer hardware 602 is in circuit communication with the memory 604 and the light source/detector 608. The computer hardware 602 includes a microprocessor, nonvolatile and/or volatile memory, digital and/or analog interface circuits, an expansion bus or slot and preferably a display. The memory 604 includes the Quantitative Sample logic (hereinafter QS logic) 606 which will be presently described. The memory 604 is preferably in the form of a removable RAM card or cartridge which may be inserted into the expansion bus or slot of the pesticide analysis device 600. The light source/detector device 608 includes a light source and a light detector. The light source is preferably a white light source and the light detector is of such construction so as to be able to detect light within at least the visible frequency spectrum (i.e., 400–700 nm wavelength range). The light source may also be constructed to emit light in a specific frequency such as 430 nm where the spectral power distribution for a particular pigment and/or pesticide is known. Moreover, the light source/detector device may include accessories such as fiber optic cables for the emission and detection of light, filters and mono-chromators. The sample compartment 610 may, as was described above, be internal or external to the spectrophotometer.

Second Illustrated Embodiment of a Pesticide Analysis Device.

Figure 6B:
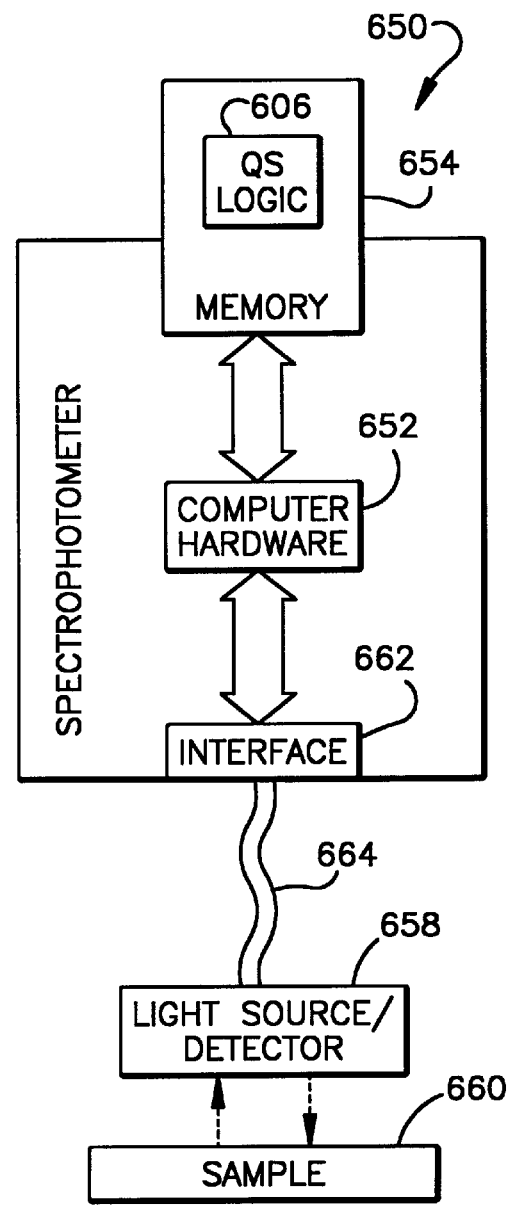

Referring now to FIG. 6B, a pesticide analysis device 650 for the dry mode and fluid of the present invention is shown. The pesticide analysis device 650 includes a spectrophotometer having computer hardware 652, a memory 654 having Quantitative Sample logic 606 and a light source/detector device 658. The pesticide analysis device 650 also includes a connecting device 665 for connecting the spectrophotometer to its light source/detector device 658 and an interface 662 for connecting the spectrophotometer to the connecting device 664. Once again, spectrophotometer devices are conventional. However, as was done in the case of the pesticide analysis device 600 of FIG. 6A, a general description of the pesticide analysis device 650 and its components illustrated in FIG. 6B will be discussed.

The computer hardware 652 is in circuit communication with the memory 654 and the light source/detector 658. The computer hardware 652 includes a microprocessor, nonvolatile and/or volatile memory, digital and/or analog interface circuits, an expansion bus or slot and preferably a display. The memory 654 includes the Quantitative Sample logic (hereinafter QS logic) 606 which will be presently described. The memory 654 is preferably in the form of a removable RAM card or cartridge which may be inserted into the expansion bus or slot of the pesticide analysis device 650. The light source/detector device 658 includes a light source and a light detector. The light source is preferably a white light source and the light detector is of such construction so as to be able to detect light within at least the visible frequency spectrum (i.e., 400–700 nm wavelength range). The light source may also be constructed to emit light in a specific frequency such as 430 nm where the spectral power distribution for a particular pigment and/or pesticide is known. Moreover, the light source/detector device 658 may be included within the spectrophotometer device 650 and the connecting device 664 may include fiber optic cables for the emission and detection of light by the light source/detector 658, filters and mono-chromators. Again, such configurations are well known in the art. A characteristic quality of the pesticide analysis device 650 is that it is of a portable nature allowing for in-the-field inspection of samples. The light source/detector 658 and/or connecting device 665 are constructed such that they may be held in the hand of the user and positioned at or near a sample to be tested. With such a portable pesticide analysis device, one may analyze leaves still on planted plants, individual seeds, fertilizers, papers and any other matter which has been coated with a fluorescent pesticide/pigment mixture of the present invention.

QS Logic

Figure 7:
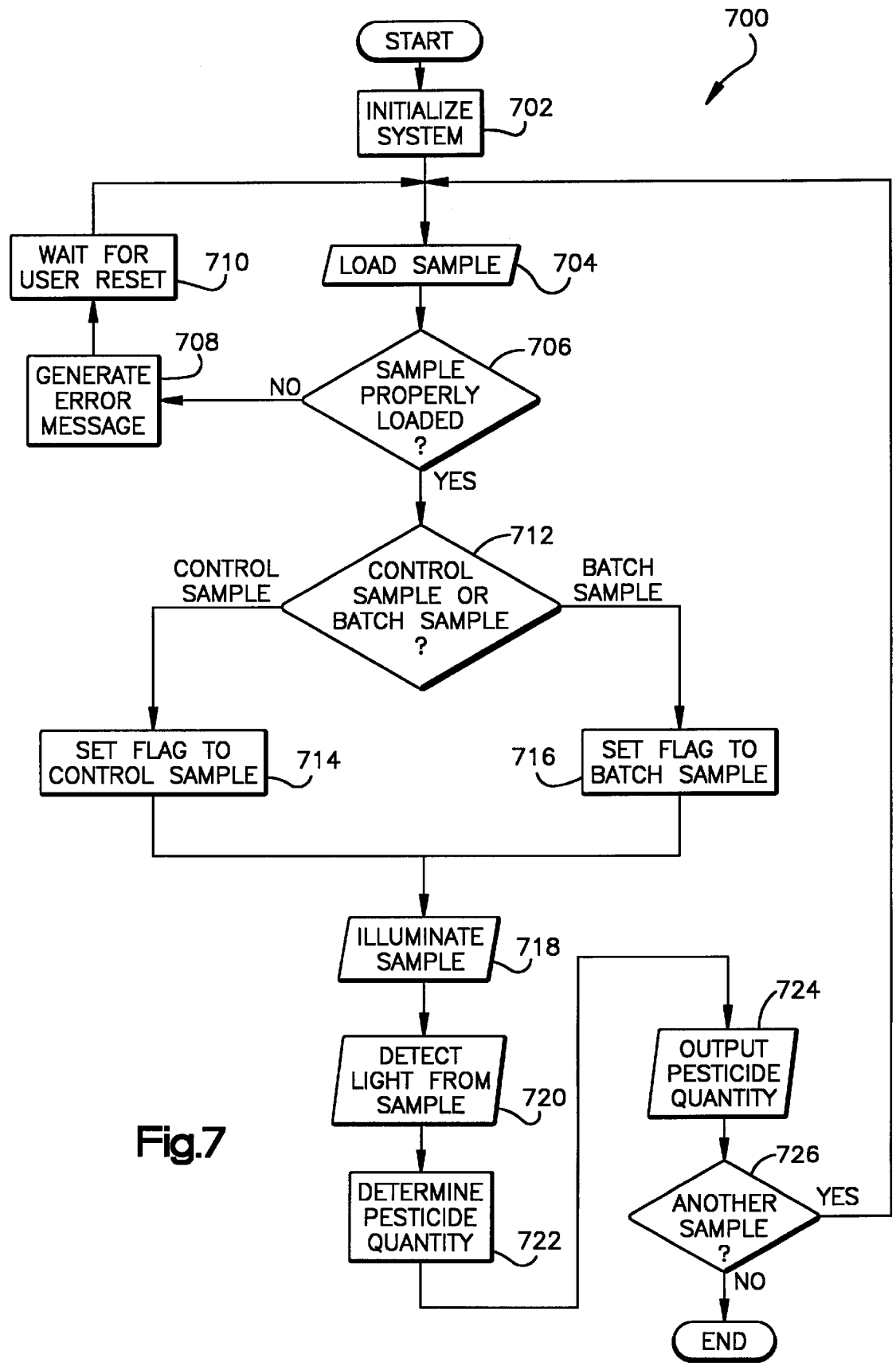
FIG. 7 illustrates the QS logic of the present invention that is employed by the pesticide analysis devices of FIGS. 6A and 6B.

FIG. 7 illustrates the QS logic 700 of the present invention that is employed by the pesticide analysis devices of FIGS. 6A and 6B. The logic begins in step 702 where the pesticide analysis device is initialized. Initialization involves the input of user parameters (to be presently discussed) and the setting of system variables and devices to their initial or start-up value. The initialization step 702 may also include a diagnostic procedure to determine if all components are operating properly. After step 702, the logic advances to step 704 where a sample is loaded for analysis. As was described earlier, the sample is placed in the sample compartment which is then placed in positioned for analysis. After step 704, the logic proceeds to step 706 where it determines whether the sample compartment and/or sample have been properly loaded or positioned for analysis. It the sample compartment and/or sample have not been properly loaded or positioned for analysis, the logic proceeds to step 708. In step 708, the logic generates an error message, which is properly displayed to the user, that the sample department and/or sample have not been properly loaded or positioned. After step 708, the logic advances to step 710 where it waits for the sample compartment and/or sample to be re-loaded or re-positioned. After the sample compartment and/or sample have in re-loaded or re-positioned, the logic loops back to step 704. If the sample has in properly loaded, the logic advances to step 712.

In step 712, the logic tests to determine whether the present sample is a control sample or a batch sample. As mentioned above, during system initialization, the user enters operating parameter data, among which is whether the current sample is a control sample or a batch sample. A control sample is a sample whose pesticide quantity has been predetermined by the pesticide/pigment mixture manufacturer and is provided with the pesticide/pigment mixture. A batch sample is a sample which is taken from a batch of seeds which have been presently sprayed with the pesticide/pigment mixture. In practicing the present invention, the user should first analyzed the control sample as it will serve as a calibration for the spectrophotometer and as a standard against which the batch sample will be compared. However, since each spectrophotometer includes linear approximation data within its QS logic, the step of first analyzing a control sample is not necessary. A user may simply analyze a batch sample based on the linear approximation data. If the resent sample is a control sample, the logic advances to step 714 where a flag is set to indicate to the system that the present sample is a control sample. If the present sample is a batch sample, the logic advances to step 716 where a flag is set to indicate to the system that the present sample is a batch sample.

After either step 714 or step 716, the logic advances to step 718. In step 718, the sample is illuminated by the light source. In step 720, the light reflected from or transmitted by the sample is detected by the light detector and converted into data for processing. After step 720, the logic proceeds to step 722 where the quantity of pesticide is determined and stored in memory. The spectrophotometer of the present invention may be programmed to analyzed the sample a plurality of times so to determined a statistic average upon which the quantity of pesticide is based. Step 722 is described in further detail and FIG. 8. After step 722, the logic advances to step 724 where the quantity of pesticide determined from step 722 is output to a display device. After step 724, the logic proceeds to step 726. In step 726, the logic queries the user to determine whether another batch sample or control sample is to be analyzed. If so, the logic loops back to step 704. If there are no other samples to the analyzed, the logic ends.

Figure 8:
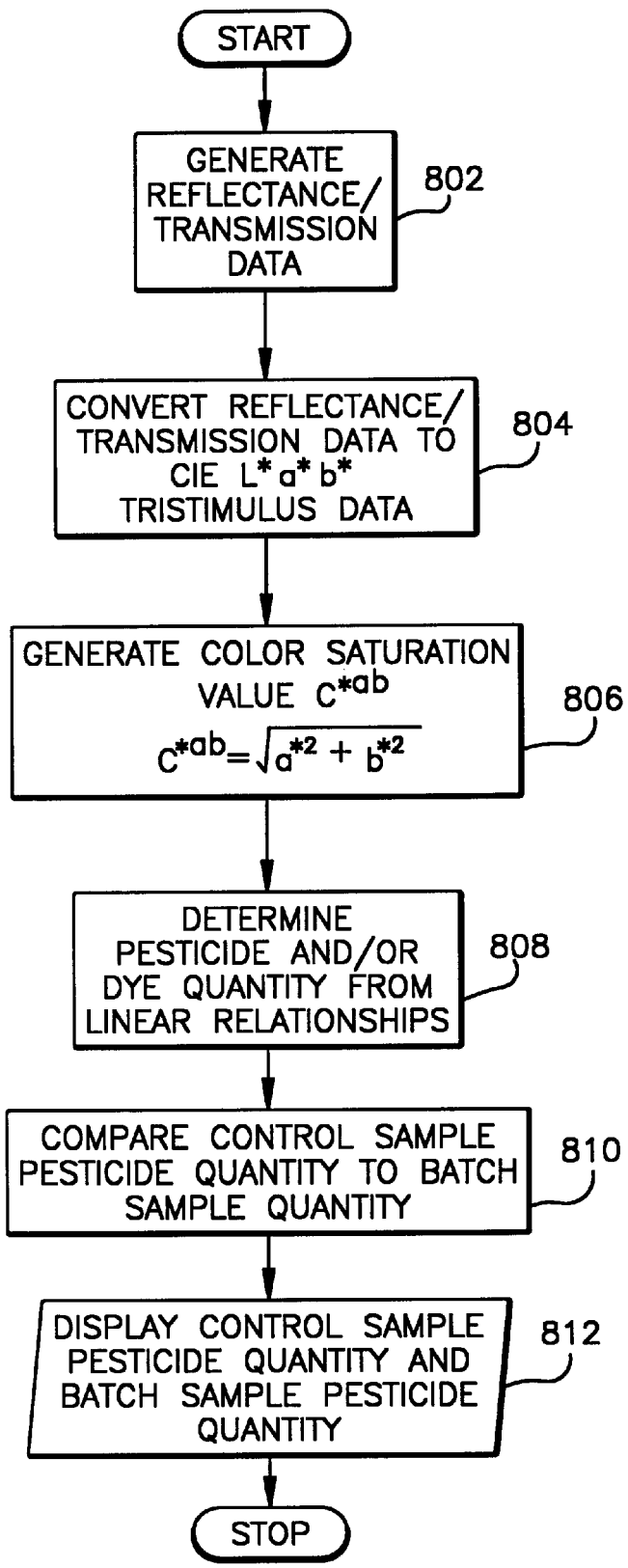
FIG. 8 illustrates the QS logic step of determining pesticide quantity from the spectral data obtained by the devices of FIGS. 6A and 6B.

Referring now to FIG. 8, the QS logic step of determining the quantity of pesticide shown in step 722 of FIG. 7 will now be described in more detail. The logic starts in step 802 where reflectance or transmission data, depending on whether a dry mode pesticide analysis or a fluid mode pesticide analysis was performed, is generated from the light detected by the light detector. The reflectance or transmission data indicates the intensity of the light across the range of 400 to 700 nm wavelengths. After step 802, the logic advances to step 804. In step 804, the reflectance or transmission data is converted to tristimulus data (discussed above) from which CIE L* a* b* uniform color space data is generated. After step 804, the logic proceeds to step 806 where the color saturation value $C^{*ab}$ (e.g., delta C) is determined from equation (2). Once the color saturation (e.g., delta C) has been determined in step 806, the logic proceeds to step 808. In step 808, the logic determines the quantity of pesticide and/or pigment from a linear approximation formula which is included within the QS logic. The quantity of pesticide is then stored in memory as either a control quantity, if the present sample was a control sample, or a batch quantity, if the present sample was a batch sample. After step 808, the logic advances to step 810. It should be noted that the logic advances to step 810 only if a control sample has been previously analyzed, otherwise the logic advances to step 812 where the quantity of pesticide for the present sample is displayed. In step 810, the logic compares the quantity of pesticide associated with the batch sample to the quantity of pesticide associated with the control sample. After step 810, the logic advances to step 812 where it displays the quantity of pesticide associated with the control sample and the quantity of pesticide associated with the batch sample. Various other data may be generated from the comparison in step 810. For example, the logic may generate "over" or "under" data or the logic may generate correction data. After step 812, the logic ends.

EXAMPLES

Referring now to FIG. 9, a table illustrating experimental data obtained by the dry mode pesticide analysis procedure on cotton seeds for the SATURN YELLOW™, FIRE ORANGE™ and CORONA MAGENTA™ pigments is shown. The results illustrate, among other things, the linearity of the relation data as applied to a "white tile" standard and an uncoated seed sample.

Example One: SATURN YELLOW™ Pigment

The dry mode pesticide analysis involves the use of a MINOLTA CM 508 D spectrophotometer, the pesticide GOUCHO™ and the pigment SATURN YELLOW™. The "A 96C 10" and "B 96C 10" designate two varieties of cotton seeds. The "(- White)" designation indicates the coated seed sample was tested against a white NIST calibrated tile. The "(- Black)" designation indicates the coated seed sample was tested against an uncoated seed sample. A glass container was filled with the coated seed sample such that substantially all of the light from the spectrophotometer was incident on the seed sample. The seed sample was then illuminated with white light and the reflected light in the 400 to 700 nm was detected to determine the color saturation value. This procedure several times so that a statistical average of the saturation value was determined. The average saturation value was then used by the QS logic to determine a quantity of pesticide. This procedure was then performed for varying quantities of pesticide and SATURN YELLOW™ pigments. The tests results are illustrated in FIG. 9.

Example Two: FIRE ORANGE™ Pigment

The dry mode pesticide analysis involves the use of a MINOLTA CM 508 D spectrophotometer, the pesticide GOUCHO® and the pigment FIRE ORANGE™. The "A 96C10" and "B 96C10" designate two varieties of cotton seeds. The "(- White)" designation indicates the coated seed sample was tested against a white NIST calibrated tile. The "(- Black)" designation indicates the coated seed sample was tested against an uncoated seed sample. A glass container was filled with the coated seed sample such that substantially all of the light from the spectrophotometer was incident on the seed sample. The seed sample was then illuminated with white light and the reflected light in the 400 to 700 nm was detected to determine the color saturation value. This procedure several times so that a statistical average of the saturation value was determined. The average saturation value was then used by the QS logic to determine a quantity of pesticide. This procedure was then performed for varying quantities of pesticide and FIRE ORANGE™. The tests results are illustrated in FIG. 9.

Example Three: CORONA MAGENTA™ Pigment

The dry mode pesticide analysis involves the use of a MINOLTA CM 508 D spectrophotometer, the pesticide GOUCHO® and the pigment CORONA MAGNETA™. The "A 96C 10" and "B 96C 10" designate two varieties of cotton seeds. The "(- White)" designation indicates the coated seed sample was tested against a white NIST calibrated tile. The "(- Black)" designation indicates the coated seed sample was tested against an uncoated seed sample. A glass container was filled with the coated seed sample such that substantially all of the light from the spectrophotometer was incident on the seed sample. The seed sample was then illuminated with white light and the reflected light in the 400 to 700 nm was detected to determine the color saturation value. This procedure several times so that a statistical average of the saturation value was determined. The average saturation value was then used by the QS logic to determine a quantity of pesticide. This procedure was then performed for varying quantities of pesticide and CORONA MAGENTA™. The tests results are illustrated in FIG. 9.

The error ranges in FIG. 9 may be reduced by modification of the calibration data set to start at 0.50 fluid ounces and ending with 8.00 fluid ounces.

While the present invention has been illustrated by the description of embodiments thereof, and while the embodiments have been described in considerable detail, it is not the intention of application to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

I claim:

1. A method for determining the quantity of pesticide in a plurality of seeds, the method comprising the steps of:
   (a) illuminating a pigment mixture present on the plurality of seeds which include a coating having a pesticide and a pigment mixture;
   (b) detecting the light reflected from the illuminated pigment mixture; and
   (c) relating the light reflected from the illuminated pigment mixture to a quantity of pesticide.

2. The method of claim 1 further comprising the step of removing the pigment mixture from a plurality of seeds having a coating that includes a pesticide and a pigment by adding a solvent to the plurality of seeds.

3. The method of claim 2 further comprising the step of waiting, for at least a minimum predetermined time interval, after adding the solvent to the plurality of seeds.

4. The method of claim 1 wherein the step of illuminating a pigment mixture derived from a plurality of seeds having a coating that includes a pesticide and a pigment comprises the step of illuminating the pigment mixture with electromagnetic radiation having a frequency within the range of 200–800 nm.

5. The method of claim 1 wherein the step of relating the light reflected from the illuminated pigment mixture to a quantity of pesticide comprises the step of determining a color saturation level of the light reflected from the illuminated pigment mixture.

6. The method of claim 5 wherein the step of relating the light reflected from the illuminated pigment mixture to a quantity of pesticide further comprises the step of relating the color saturation level of the light reflected from the illuminated pigment mixture to a quantity of pesticide.

7. A method for determining the relationship between a quantity of pigment and a quantity of pesticide, the method comprising the steps of:
   (a) mixing a known quantity of pigment with a known quantity of pesticide;
   (b) applying the mixture to a seed sample;
   (c) removing a substantial amount of the pigment from the mixture which has adhered to the plurality of seeds;
   (d) determining a quantity of pigment from the removed amount of pigment; and
   (e) determining a quantity of pesticide from the determined quantity of pigment.

8. The method of claim 7 wherein the step of removing a substantial amount of pigment from the mixture which has adhered to the plurality of seeds comprises the step of adding a solvent to the plurality of seeds.

9. The method of claim 7 wherein the step of determining a quantity of pigment from the removed amount of pigment comprises the step of determining a color saturation level of the removed amount of pigment.

10. The method of claim 9 wherein the step of determining a color saturation level of the removed amount of pigment comprises the step of illuminating the removed amount of pigment.

11. The method of claim 10 wherein the step of determining a color saturation level of the removed amount of pigment further comprises the step of detecting the light reflected from the illuminated, removed amount of pigment.

12. The method of claim 10 wherein the step of illuminating the removed amount of pigment comprises the step of illuminating the removed amount of pigment with electromagnetic radiation having a frequency in the range of 400–700 nm.

13. A device for determining the amount of pesticide in a sample, the device comprising:
   (a) computer hardware for the input, output and processing of digital and analog signals;
   (b) a light source for emitting electromagnetic radiation;
   (c) a light detector for detecting electromagnetic radiation; and
   (d) logic for determining the amount of pesticide in a sample, wherein said logic comprises logic for determining a color saturation level of the sample.

14. The device of claim 13 wherein the logic for determining the amount of pesticide in a sample is included within a removable memory device.

15. The device of claim 13 wherein the logic for determining the amount of pesticide in a sample further comprises logic for relating the color saturation level to a quantity of pigment.

16. The device of claim 15 wherein the logic for determining the amount of pesticide in a sample further comprises logic for relating the quantity of pigment to a quantity of pesticide.

17. The device of claim 15 wherein the logic for relating the color saturation, level to a quantity of pigment comprises logic for applying a predetermined linear approximation to determine the quantity of pigment.

18. The device of claim 16 wherein the logic for relating the quantity of pigment to a quantity of pesticide comprises logic for applying a predetermined linear approximation to determine the quantity of pesticide.

19. The device of claim 13 wherein the computer hardware, light source, light detector and logic for determining the amount of pesticide in a sample are comprised within a spectrophotometer.

20. The device of claim 13 further comprising logic for transforming a first color space to a second color space.

* * * * *